United States Patent [19]

Surmatis et al.

[11] 3,974,181

[45] Aug. 10, 1976

[54] TRIMETHYL-1,4-DIOXASPIRO[4,5]DEC-7-EN-8-METHANOL

[75] Inventors: Joseph Donald Surmatis; Armin Walser, both of West Caldwell, N.J.

[73] Assignee: Hoffmann-La Roche Inc., Nutley, N.J.

[22] Filed: Jan. 6, 1975

[21] Appl. No.: 538,621

Related U.S. Application Data

[62] Division of Ser. No. 325,690, Jan. 22, 1973, Pat. No. 3,879,424, which is a division of Ser. No. 163,436, July 16, 1971, Pat. No. 3,732,214, which is a division of Ser. No. 55,565, July 19, 1970, Pat. No. 3,661,997, which is a division of Ser. No. 617,787, Feb. 23, 1967, Pat. No. 3,558,712.

[52] U.S. Cl. ............................................ 260/340.9
[51] Int. Cl.$^2$ ....................................... C07D 317/10

[58] Field of Search .................................. 260/340.9

[56] References Cited
UNITED STATES PATENTS

| | | | |
|---|---|---|---|
| 3,466,331 | 9/1969 | Surmatis et al. ................ | 260/586 C |
| 3,875,241 | 4/1975 | Corbier et al. ................ | 260/340.9 X |
| 3,879,424 | 4/1975 | Surmatis et al. ................ | 260/340.9 |

*Primary Examiner*—Ethel G. Love
*Attorney, Agent, or Firm*—Samuel L. Welt; Bernard S. Leon; William H. Epstein

[57] ABSTRACT

The compound 7,9,9-trimethyl-1,4-dioxaspiro [4,5] dec-7-en-8-methanol an intermediate in the preparation of Zeaxanthin and Xanthophyll, known coloring agents for foodstuffs.

1 Claim, No Drawings

TRIMETHYL-1,4-DIOXASPIRO[4,5]DEC-7-EN-8-METHANOL

CROSS REFERENCE TO RELATED APPLICATIONS

This application is a divisional application of Ser. No. 325,690, now U.S. Pat. No. 3,879,424, issued Jan. 22, 1973, which in turn is a divisional of Ser. No. 163,436, filed July 16, 1971, now U.S. Pat. No. 3,732,214, issued May 8, 1973, which in turn is a divisional application of Ser. No. 55,565, filed July 19, 1970, now U.S. Pat. No. 3,661,997, issued May 9, 1972. U.S. application Ser. No. 55,565 is a divisional application of Ser. No. 617,787, filed Feb. 23, 1967, now U.S. Pat. No. 3,558,712 issued Jan. 26, 1971.

BACKGROUND OF THE INVENTION

This invention is directed to a method whereby zeaxanthins and xanthophylls can be synthetically produced without the necessity for isolating these materials from their natural source.

Zeaxanthin and xanthophylls are widely distributed in nature, occurring in green plants, as well as in the egg yolks and in animal fats. It is well known that during the winter months when the diet of domestic animals is low in zeaxanthins and xanthophyll, the color of egg yolks, milk fat and the fat of fowls becomes bleached, which is caused by the lack of zeaxanthin and xanthophyll pigments in the diet of animals. It is also well known that this lack in the diet of animals can be readily corrected by an addition of zeaxanthin or xanthophylls to animal feeds during the winter months. Furthermore, zeaxanthin and xanthophylls serve as valuable yellow food and beverage colorants for human consumption. Therefore, these colorants are widely utilized in coloring foodstuffs, including beverages, cosmetic and pharmaceutical preparations.

In the past, zeaxanthins and xanthophylls have been produced by isolating these materials from their natural source, such as green plants and vegetables. This procedure is extremely disadvantageous due to the fact that these coloring materials occur in small amounts in the green plants or vegetables must be utilized in order to isolate a small amount of these coloring materials. Additionally, the process whereby these coloring materials are isolated from green plants and vegetables is extremely cumbersome and uneconomical. Up until the present time, there has been no economic procedure for directly chemically synthesizing these coloring materials without isolating these materials from their natural source. Therefore, it has been long desired in the art to provide a method for chemically synthesizing these coloring materials so as to eliminate the necessity of isolating these materials from their natural source.

SUMMARY OF THE INVENTION

In accordance with this invention, it has been found that new and novel compounds of the formula:

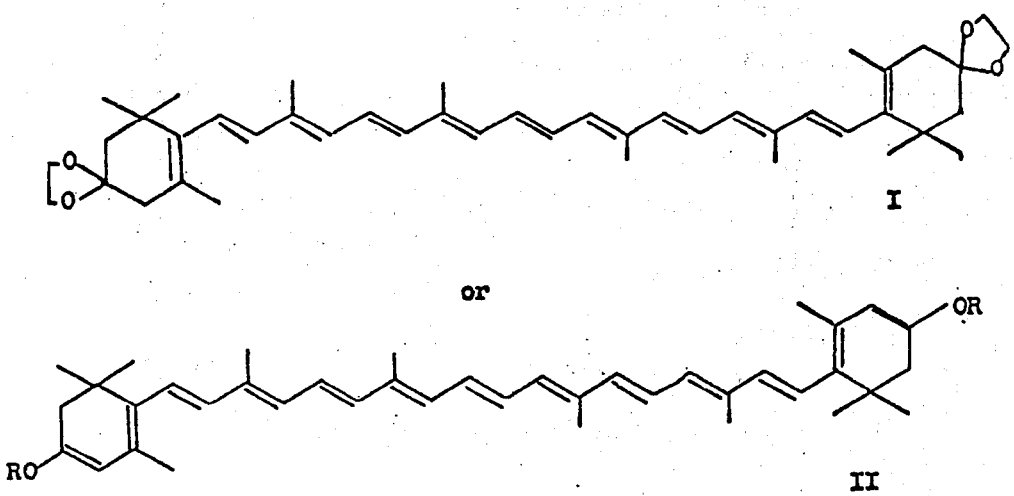

wherein R is lower alkyl, which are valuable intermediates in the chemical synthesis of xanthophylls and zeaxanthins, can be directly synthesized from novel intermediates

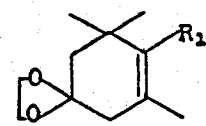

wherein $R_1$ is —COOR, —CH$_2$OH or —CHO, and:

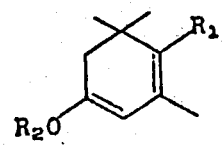

wherein $R_1$ is as above and $R_2$ is a lower alkyl, which is produced through the condensation of mesityl oxide and aceto acetic ester. In this manner coloring materials such as the zeaxanthins and xanthophylls can be directly synthesized from the condensation product of mesityl oxide and aceto-acetic ester without the necessity of isolating these materials from their natural source. Hence the use of these novel intermediates of formula I and II provides the first synthetic method of preparing zeaxanthin and xanthophyll, thereby eliminating the costly and cumbersome process of isolating these coloring materials from their natural source.

In accordance with this invention, the intermediate of formula III can be utilized to produce new and novel coloring materials of the formula:

by means of producing an intermediate of the formula:

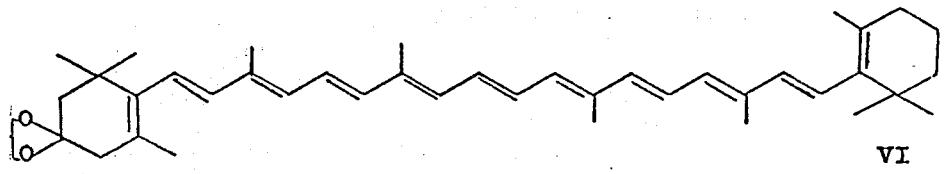

VI from the compound of formula III above. These coloring agents can be utilized to color foodstuffs, cosmetic and pharmaceutical preparations in the same manner as beta carotene. Therefore, this invention provides a new means for producing new coloring materials for foodstuffs, cosmetic and pharmaceutical preparations.

DETAILED DESCRIPTION OF THE INVENTION

The novel intermediate of Formula II above can be produced by the following reaction sequence.

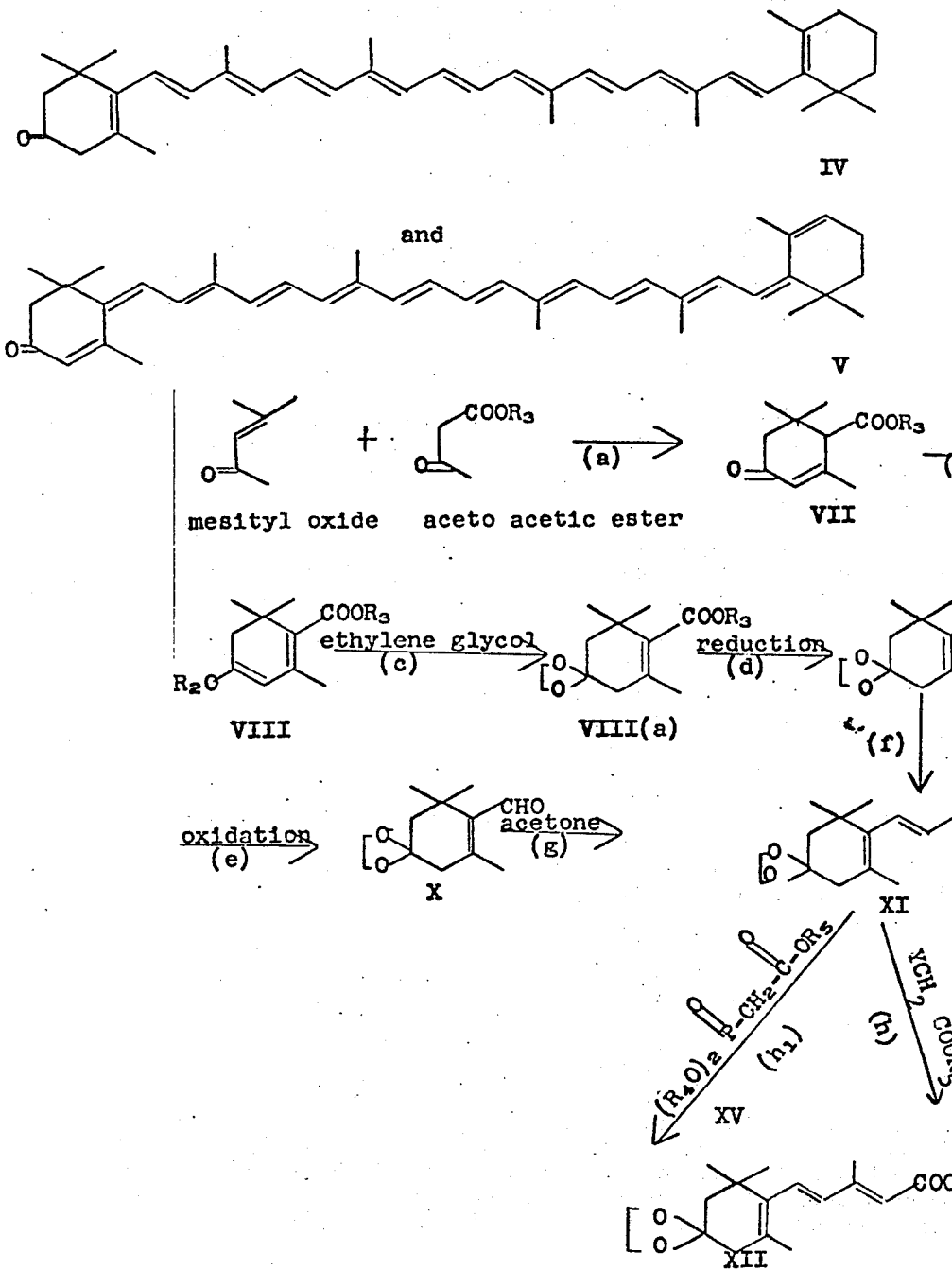

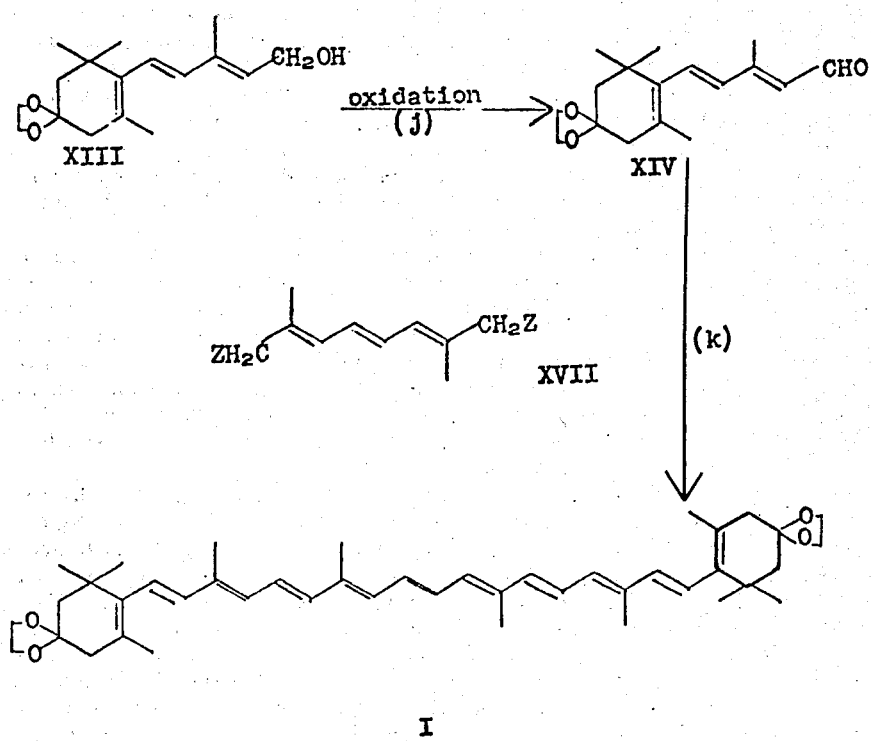

wherein $R_2$, $R_3$, and $R_4$ and $R_5$ are lower alkyl radicals, Y is a halogen and Z is selected from the group consisting of $(R_6)_3$ XP— and $(OR_6)_2$ OP— radicals, $R_6$ is selected from the group consisting of lower alkyl radicals, an aryl radical such as phenyl, naphthyl, etc. and aralkyl radical containing from 7 to 15 carbon atoms such as benzyl, etc. and X is an anion of a mineral acid such as I⁻ BR⁻, Cl⁻ and $HSO_4^-$.

The condensation as in step (a) of mesityl oxide and acetoacetic acid ester to form lower alkyl esters of 3,5,5-trimethyl-2-cyclohexen-1-on-4 carboxylic acid (formula VII above) is carried out by condensing one mole of mesityl oxide with one mole of acetic acid ester at reflux temperature in the presence of an inert organic solvent utilizing an acid catalyst such as an acid condensing agent. Any conventional inert organic solvent, preferably those which are immisible with water, can be utilized in carrying out this reaction. Typical organic solvents which can be utilized in carrying out this reaction include chloroform, carbon tetrachloride, hydrocarbon solvents such as benzene, heptane etc. In carrying out this reaction, any conventional acid catalyst can be utilized. The acid condensing agent or catalysts which can be utilized in accordance with this invention are preferably strong acids such as the mineral acids, Lewis acids, borontrifluoride, zinc chloride, etc., strong acedic organic acids such as toluene sulfonic acid, oxalic acid, trichloro acetic acid, etc. In carrying out this condensation reaction, the reflux temperature of the solvent media should be utilized. These temperatures can vary from 50°C. to 150°C. depending upon the solvent utilized. While it is preferred to utilize mesityl oxide and aceto-acetic ester in stoichometric proportions, a molar excess of either mesityl oxide or aceto-acetic ester can be utilized in carrying out this reaction.

The conversion of the ester compounds of formula VII above to the etherified carboxylic acid ester compounds of formula VIII above is carried out by treating the compounds of formula VII above with a lower alkyl tri ester of formic acid in the presence of an inorganic or mineral acid. This reaction is preferably carried out in an organic solvent. Any of the aforementioned solvents can be utilized in carrying out this reaction. Any of the conventional mineral acids such as sulfuric acid, hydrochloric acid, hydrobromic acid, phosphoric acid, etc. can be utilized in this reaction. Typical esters of formic acid which can be utilized in carrying out this reaction include, triethyl orthformate, trimethyl orthoformate, triisopropyl orthoformate, etc. In carrying out this reaction, temperature and pressure are not critical and the conversion of compounds of formula VII to compounds of formula VIII above can be effected at room temperature and at atmospheric pressure or at elevated or reduced temperatures and/or elevated or reduced pressure. Upon treatment of the compound of formula VII above with the trialkyl ester of orthoformic acid, it was surprisingly found that in addition to the keto group being converted to an ether group, the double bond in the 2 and 3 position was shifted to the 1 – 2 position with an additional double bond being formed in the 3 and 4 position as in formula VIII above.

The ether compound of formula VIII above is converted to the dioxy carboxylic acid ester of formula VIII(a) above by treating compounds of formula VIII above with ethylene glycol at elevated temperatures in an inert organic solvent medium. Any of the conventional inorganic solvents such as the aforementioned solvents can be utilized in carrying out this reaction. This reaction is carried out by utilizing an acid catalyst such as any of the aforementioned acid catalysts or condensing agents. In carrying out this reaction, temperatures of above a temperature of about 60°C. should be utilized. The highest temperature which can be utilized in carrying out this reacting will depend upon the reflux temperature of the reaction medium. Generally, in carrying out this reacting, temperatures of from about 60°C. to about 140°C. can be advantageously employed depending upon the solvent utilized. The ethylene glycol which is utilized in the reaction of step (c) should be present so as to provide 1 mole of ethylene glycol per mole of the compound of formula VIII. If desired, a molar excess of ethylene glycol or the compound of formula VIII can be present in the reaction medium. The reaction of ethylene glycol with the compound of formula VIII converts the ether group to a dioxo aspiro group while removing the double bond in the 3 and 4 position on the benzene ring to produce the compounds of formula VIII(a).

Upon treating the compounds of formula VIII(a) with an alkali metal aluminum hydride reducing agent such as lithium aluminum hydride, sodium aluminum hydride, etc., the ester radical on the compound of formula VIII(a) is reduced to a hydroxy radical to produce the corresponding dioxy hydroxy compound of formula IX without any reduction of the double bonds or dioxy groups within the compound of formula VIII(a). The reduction with the alkali metal aluminum hydride reducing agent is preferably carried out under anhydrous conditions in the presence of an inert organic solvent such as any of the aforementioned organic solvents. The reaction is suitably carried out at room temperature. However, temperatures of from about −20°C. to about 80°C. can be utilized in carrying out this reaction.

The dioxy hydroxy compound of formula IX can be converted to the corresponding dioxy aldehyde compound of formula X by means of oxidation. Any conventional oxidation technique can be utilized to oxidize the compound of formula IX above to the compound of formula X. A method of oxidation which can be utilized includes treating compounds of formula IX above with an oxidizing agent in the presence of an inert organic solvent. Any conventional oxidizing agent can be utilized in carrying out this reaction. Typical oxidizing agents which can be utilized in this reaction include mercuric oxide, potassium dichromate, manganese dioxide, chromium trioxide, etc. These oxidation reactions are generally carried out in the presence of an inert organic solvent such as any of the solvents mentioned hereinbefore. In carrying out this reaction, temperature and pressure are not critical and this oxidation reaction can be effected at room temperature and at atmospheric pressure or at elevated or reduced temperatures and/or reduced or raised pressure.

The dioxy aldehyde compound of formula X above can be converted into the ionone compound of formula XI above by means of condensing one mole of the compound of formula X with one mole of acetone as in step (g). This condensation reaction should be carried out in the presence of a strong base, preferably an alkali metal hydride such as potassium hydride, sodium hydroxide, lithium hydroxide, calcium hydroxide, etc. Alkali metal hydrides such as sodium hydride, potassium hydride, etc. and alkali metal amides such as sodium amide can be utilized as the base. Any conventional alkali condensation agent can be utilized in carrying out this reaction. In carrying out the condensation reaction of step (g), temperature and pressure are not critical so that the reaction can be carried out at room temperature. However, if desired, elevated or reduced temperatures can be utilized as well as elevated or reduced pressure. The condensation reaction of step (g) is carried out by condensing 1 mole of the compound of formula X with 1 mole of acetone. Generally, it is preferred to utilize acetone as the solvent medium, thereby utilizing an excess of acetone in the reaction medium. However, if desired, this condensation reaction can be carried out in the presence of any conventional organic solvent, such as the solvents hereinbefore mentioned.

In accordance with this invention, the dioxy hydroxy compound of formula IX above can be directly converted into the ionone compound of formula XI above without the necessity of oxidizing the compound of formula IX above to the compound of formula X above. This can be done by reacting the compound of formula IX above with acetone in the presence of aluminum isopropoxide as in step (f). This reaction is preferably carried out by utilizing acetone as the solvent or reaction media while maintaining the temperature at from about 60°C. to about 65°C. The aluminum isopropoxide in step (f) acts both as an oxidizing agent and catalyst so that the compound of formula IX above is directly converted in the presence of acetone into the ionone compound of formula XI above. Generally, in carrying out the reaction of step (f), catalytic quantities of aluminum isopropoxide should be present per mole of the compound of formula IX above, i.e. about 0.1 mole of aluminum isopropoxide. If desired, from about one mole to three moles of aluminum isopropoxide per mole of the compound of formula IX above, can be utilized in carrying out this reaction.

The conversion of the ionone compound of formula XI above to the dioxy pentanoic acid ester of formula XII above can be carried out by any one of two methods as shown in steps (h) and ($h_1$). The method of step ($h_1$) is carried out by reacting a phosphorous containing compound of formula XV, above with the compound of formula XI in an inert organic solvent medium in the presence of a strong alkali or alkali condensing agent. The reaction of step ($h_1$) is carried out in a solvent medium such as ethyl ether, methanol, ethanol under substantially anhydrous conditions. Any of the alkalis or alkali condensing agents hereinbefore mentioned can be utilized in the reaction of step ($h_1$). These alkalis include sodium methoxide, sodium hydride, etc. Generally, it is preferred to utilize an organic alkali in the reaction of step ($h_1$) in order to prevent water from entering the reaction medium. In carrying out the reaction of step ($h_1$), it is preferred to react one mole of the compound of formula XI above with one mole of the compound of formula XV, above. However, if desired, a molar excess of the compound of formula XI, above or a molar excess of the compound of formula XV, above can be utilized in this reaction. In carrying out this reaction, temperature and pressure are not critical and this reaction can be effected at room temperature and atmospheric pressure or at elevated temperatures such as the reflux temperature of the solvent or reduced temperatures such as the slightly above freezing temperature of the solvent.

According to another embodiment of the invention, the compound of formula XI, above can be converted into the compound of formula XII, above by reaction with an ester of a mono halogenated acetic acid of formula XVI in an inert organic solvent in the presence of zinc metal in accordance with step (h). The reaction of step (h) can be carried out in any conventional inert organic solvent such as toluene, benzene or xylene at the reflux temperature of the solvent. The zinc metal is added to the reaction medium to provide at least one mole of the zinc in powdered form per mole of the compound of formula XI above to the reaction medium. The reaction of step (h) is carried out by reacting one mole of the compound of formula XI, above with one mole of the compound of formula XVI, above. However, if desired, a stoichometric excess of the compound of formula XI, above or the compound of formula XVI above can be utilized.

The dioxy pentanoic acid ester of formula XII, above can be recovered from the reaction media produced by either steps (h) or (h₁) by means of extracting the water soluble materials from the reaction medium with water and distilling off the organic solvent or solvents. The ester of formula XII, above is converted into the corresponding dioxy hydroxy compound of formula XIII, above by means of reduction with an alkali metal aluminum hydride reducing agent utilizing the same conditions that were utilized in connection with the reduction of the compound of the formula of VIIIa above. The dioxy hydroxy compounds of formula XIII above are then oxidized as in step (j) utilizing the same conditions that were utilized in oxidizing the compound of formula IX above, to form the corresponding dioxy pentenal compound of formula XIV above.

The dioxy pentenal compound of formula XIV above is converted into the intermediate of formula I by reacting in step (k) 2 moles of the compound of formula XIV above with one mole of the dipentavalent phosphorous compound of formula XVII in an inert organic solvent media. This reaction is conducted in the presence of a strong alkali or base, such as an alkali metal hydride, e.g., sodium hydride, potassium hydride, alkali metal amide, e.g., sodium amide, and alkali metal-lower alkoxide, preferably sodium methoxide or a solution of an alkali metal hydroxide in a lower alkanol, e.g., potassium hydroxide in methanol. Any organic solvents substantially inert to the reactants such as a lower alkanol solvent having from one to seven carbon atoms, i.e., methanol, ethanol, etc. dimethylformamide, acetonitrile or benzene can be utilized. The preferred solvents are methanol and benzene. This reaction can be carried out at room temperature. However, temperatures as high as the reflux temperature of the solvent or as low as just above the freezing point of the solvent can be employed. While carrying out the reaction of step (k), two moles of the compound of formula XIV is reacted with one mole of the compound of formula XVII above, a molar excess of the compound of formula XIV above can be present in the reaction medium.

The intermediate of formula II, above can be produced from the compound of formula VIII, above by the following reaction scheme:

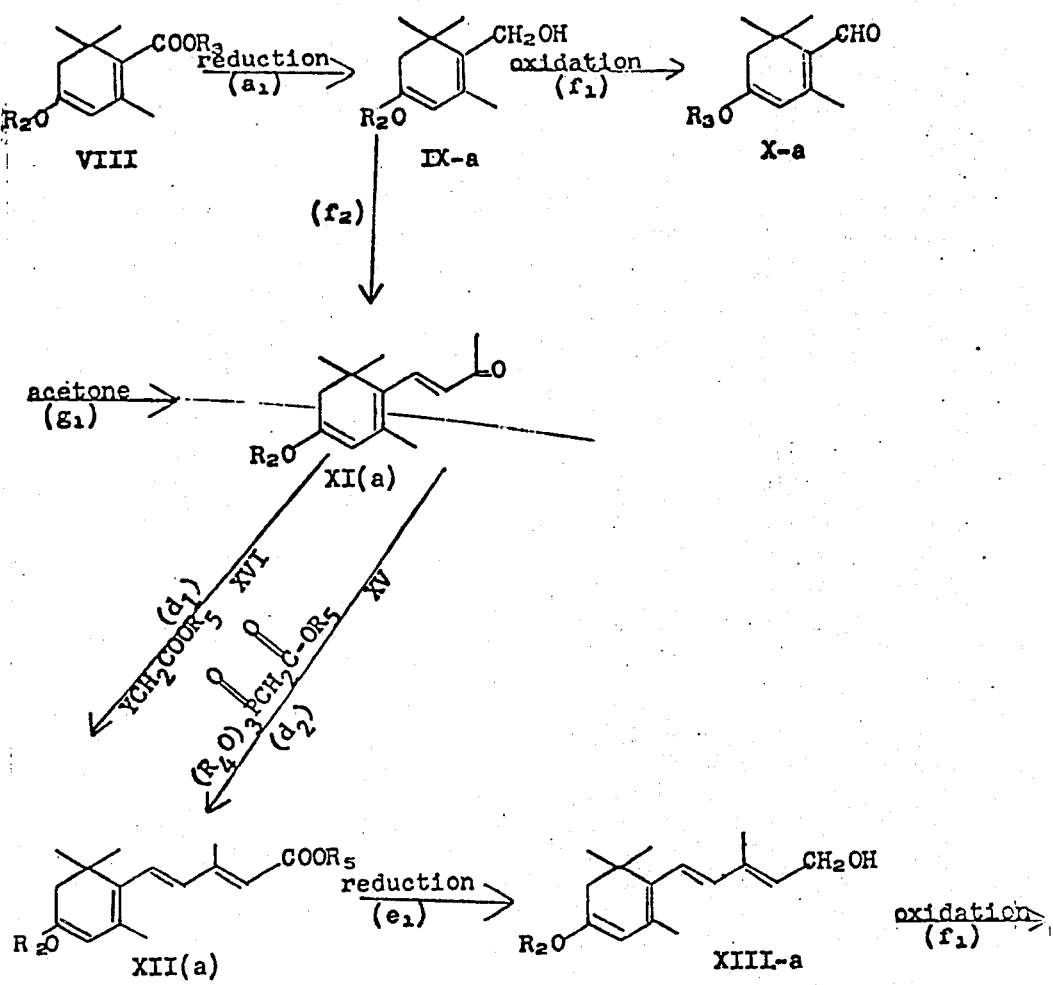

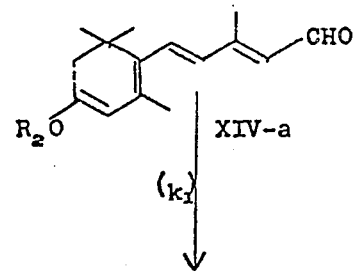

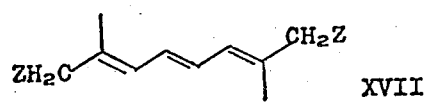

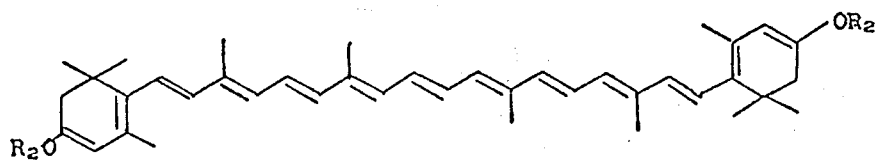

wherein $R_2$, $R_4$, $R_5$, Z and Y are as above.

The etherified carboxylic acid ester compound of formula VIII, above is converted to the intermediate of formula II by first reducing the compound of formula VIII above to the etherified hydroxy compound of formula IX-a by means of an alkali metal aluminum hydride reducing agent as in step ($a_1$). The aforementioned conditions which were utilized in step (d) in the reduction of the compound of formula VIII-a can be utilized in step ($a_1$). The hydroxy compound of formula IX-a is then oxidized by means of an oxidizing agent to form the corresponding aldehyde of compound of formula X-a above as in step ($f_1$). Any of the oxidizing agents and conditions utilized in oxidizing the compound of formula IX as in step (e) can be utilized in this reaction. In the next step ($g_1$), the aldehyde compound of formula X-a above is condensed with acetone in the same manner as in step (g) to form the etherified ionone compound of formula XI-a above. On the other hand, the ionone compound of formula XI-a above can be prepared directly from the hydroxy compound of IX-a as in step ($f_1$) by reacting the compound of IX-a with aluminum isopropoxide in acetone in the manner that compound IX above was reacted in step (f).

The ionone compound of formula XI-a is converted into the pentanoic acid ester of the compound of formula XII-a, above by reaction with the monohalogenated acetic acid ester of compound XVI as in step ($d_1$) or by reaction with the dipentavalent phosphorous compound XV above as in step ($d_2$). The reaction of step ($d_1$) is carried out in the same manner as the reaction of compound of the formula XI above with the compound of the formula XVI in step (h). The reaction of compound XI-a, above with the compound of the formula XV, above is carried out in the same manner as the reaction of compound of the formula XI with the compounds of the formula XV as in step ($h_1$). The pentanoic acid ester compound of formula XII-a which is formed as a result of either reaction steps ($d_1$) or ($d_2$) is then reduced with an alkali metal aluminum hydride in step ($e_1$) in the same manner as described hereinbefore with respect to the reduction of compound VIII-a, above in step (d). The corresponding hydroxy compound of formula XIII-a above which is formed as a result of the reduction reaction of step ($e_1$) is then oxidized by means of an oxidizing agent in step ($f_1$) to form the corresponding compound of formula XIV-a. The oxidation step ($f_1$) carried out in the same manner as described in step (e) in connection with the oxidation of compound X. The pentenal compound of formula XIV-a above, which is formed by means of oxidation of the compounds of formula XIII-a is converted into the intermediate of formula II by reacting 2 moles of the compound of formula XIV-a with one mole of the compound of formula XVII above as in step ($k_1$). This reaction is carried out in the same manner and utilizing the same conditions as in the reaction of compound XIV with compound XVII as described in connection with step (k). The intermediate II which is formed by the reaction ($k_1$) is obtained as a precipitate. Therefore, this intermediate can be easily isolated from the reaction medium, if desired.

The novel intermediates of formulae I and II above can be converted into, zeaxanthin, ϵ-zeaxanthin and xanthophyll by means of the following reaction scheme:

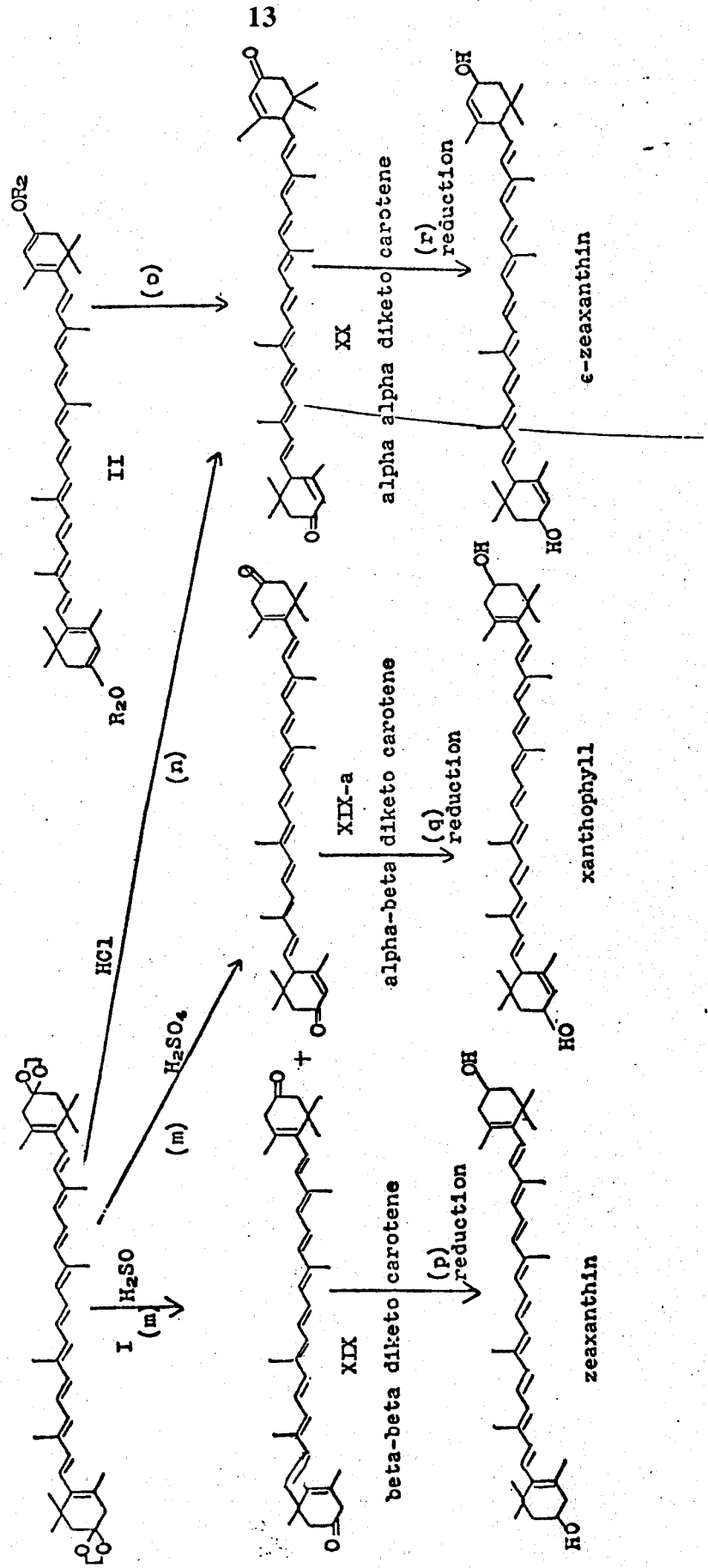

wherein $R_2$ has the meaning given hereinbefore.

The novel compounds of formula I can be converted into zeaxanthin or xanthophyll by first treating the compounds of formula I above with dilute sulfuric acid in an inert organic solvent media. It has been found that when the compounds of formula I are treated with a dilute aqueous sulfuric acid solution, in an inert organic solvent, a mixture composed of the compound of the formula XIX (beta beta diketo carotene) and the compound of the formula XIX-a (alpha beta diketo carotene) is formed. In carrying out the reaction of step (m), the aqueous solution of sulfuric acid should contain from about 1 percent by weight to about 30 percent by weight sulfuric acid based upon the weight of the aqueous solution. Concentrations of sulfuric acid above about 30 percent by weight, based upon the weight of the aqueous should be avoided since, it has been found that such high concentration tend to decompose the compound of formula I above. This reaction can be carried out at room temperature. If desired, temperatures as low as about the freezing temperature of the reaction media and as high as about 50°C. can be utilized. However, if elevated temperatures are utilized, care must be taken to see that the reaction media never goes over a temperature of 50°C., since temperatures about 50°C. tend to decompose the compound of formula I above. Any inert organic solvent capable of dissolving the compounds of formula I above can be utilized in carrying out this reaction, however, the inert organic solvent must have a boiling point below 50°C. A typical solvent mixture which can be utilized in accordance with this invention includes a mixture of methylene chloride and acetone.

The mixture of the compound of the formula XIX above and formul XIX-a above can be recovered from the reaction media by means of extraction with an organic solvent and distillation from the organic solvent. Compound of formula XIX above can be separated from the compound of formula XIX-a above by any conventional chromatographic separation such as by silica gel chromatography or by aluminum oxide chromatography. The chromatographic separation of the compounds of formula XIX and XIX-a produces 2 pure separate fractions, one of the fractions containing the compound XIX and the other fraction containing the compound XIX-a.

The compound XIX can be converted into zeaxanthin by means of treating the compound of formula XIX with a reducing agent selected from the group consisting of aluminum isopropoxide, an alkali metal or hydride such as sodium borohydride, di-isobutyl aluminum hydride, and an alkali metal aluminum hydride such as lithium aluminum hydride. Any conventional reducing conditions can be utilized to reduce the compound of formula XIX to zeaxanthin by means of utilizing the aforementioned reducing agents. In carrying out this reaction of step (p), temperature and pressure are not critical and this reaction can be effected at room temperature and atmospheric pressure or at elevated temperature such as the reflux temperature of the solvent and or reduced pressure. The reduction reaction is generally carried out in the presence of an inert organic solvent. Any conventional organic solvent can be utilized to carry out this reaction. In accordance with this invention, it has been found that the aforementioned reducing agents reduce the keto groups in the compound of formula XIX to hydroxy groups without effecting any change of the double bonds within the compound of formula XIX. In this manner, zeaxanthin can easily be produced from compounds of formula XIX.

The compound of formula XIX-a can be converted to xanthophyll by means of treating the compounds of formula XIX-a with a reducing agent selected from the group consisting of aluminum isopropoxide, an alkali metal borohydride such as sodium borohydride, di-isobutyl aluminum hydride, and an alkali metal aluminum hydride such as lithium aluminum hydride as in step (q). The same reducing conditions that are utilized in step (p) are utilized in step (q) to convert the compounds of formula XIX-a to xanthophyll. It has been found that when a compound of formula XIX-a is treated with any of the aforementioned reducing agents, the keto groups within the compound of formula XIX-a are reduced to the hydroxy groups without the double bonds contained therein being effected. In this manner, xanthophyll is easily produced from the compound of formula XIX-a.

On the other hand, the mixture of XIX-a and XIX can be reduced without separation to form a mixture of zeaxanthin and xanthophylls which can be used as a pigment for animal feed supplements. This mixture represents the mixture as it is isolated in nature. The reduced mixture can be used as a coloring agent in the same manner as their individual components.

The compound of formula I can be converted to xanthophyll by means of first treating the compound of formula I with a concentrated aqueous solution of hydrochloric acid to form the compound of formula XX above. This reaction is carried out in the presence of a mixture of organic solvent, at least one of the solvents being able to dissolve water. A typical solvent mixture which can be utilized to carry out the reaction of step (m) is a mixture of ethyl alcohol and methylene chloride. In carrying out the reaction of step (m), temperature and pressure are not critical and the reaction can be effected at room temperature. However, if desired, elevated or reduced temperatures can be utilized in carrying out this reaction. In carrying out this reaction, care must be taken not to exceed a temperature of 50°C. since decomposition of the compound of formula I can occur when such high temperatures are utilized. The reaction of the compound of formula I with a concentrated solution of HCl, that is an aqueous solution containing from about 18 percent by weight to about 37 percent by weight HCl, based, upon the weight of the aqueous solution, simultaneously converts the dioxaspiro groups contained within the compound of formula I to keto groups while simultaneously shifting the double bonds from the 1, 2 and 1' 2' positions to the 2 3 and 2' 3' positions. On the other hand, it has been found that when the compounds of formula I above are reacted with dilute sulfuric acid, only the double bond in the 1 2 position is converted to the 2 3 position. Hence, by means of the reaction with concentrated HCl, the compounds of formula I are easily converted into the compounds of formula XX which are intermediates for zeaxanthin.

The novel compounds of formula II can be easily converted into the compounds of formula XX by any convenentional acid hydrolysis procedure. In carrying out the acid hydrolysis, any conventional inorganic acid can be utilized. Furthermore, this reaction can be carried out in any conventional inert organic solvent. In carrying out the acid hydrolysis reaction of step (o), to convert the compound of formula II to the compound of formula XX, temperature and pressure are not critical. The reaction can be carried out at room temperature and at atmospheric pressure. However, reduced or elevated temperatures and/or reduced or elevated pressures can be utilized in carrying out this reaction.

The conversion of the compound of the formula XX to ε-zeaxanthin is carried out by treating the formula of the compound XX with a reducing agent selected from the group consisting of aluminum isopropoxide, alkali metal borohydride, di-isobutyl aluminum hydride and an alkali metal aluminum hydride. The reduction of the compound XX in step (r) is carried out in the same manner as the reduction of the compound of the formula XIX above in step (p). The reduction of the compound of the formula XX in step (r) converts the keto groups directly to hydroxy groups without effecting any of the double bonds contained within the compound of formula XX. In this manner, a compound of the formula XX is converted to ε-zeaxanthin.

In accordance with this invention, it has been found that the compound of the formula XX above and ε-zeaxanthin can be utilized for coloring foodstuffs, pharmaceutical and cosmetic preparations. The compound of formula XX, ε-zeaxanthin both impart a yellow color to the foodstuffs, pharmaceutical and cosmetic preparations into which they are incorporated. These materials can be incorporated into foodstuffs, pharmaceutical and cosmetic preparations in the same way as beta-carotene.

In accordance with this invention, a new coloring material, 3-oxo-beta carotene, for foodstuffs, pharmaceutical and cosmetic preparations can be synthesized from the compound of formula XIV above by means of the following reaction scheme:

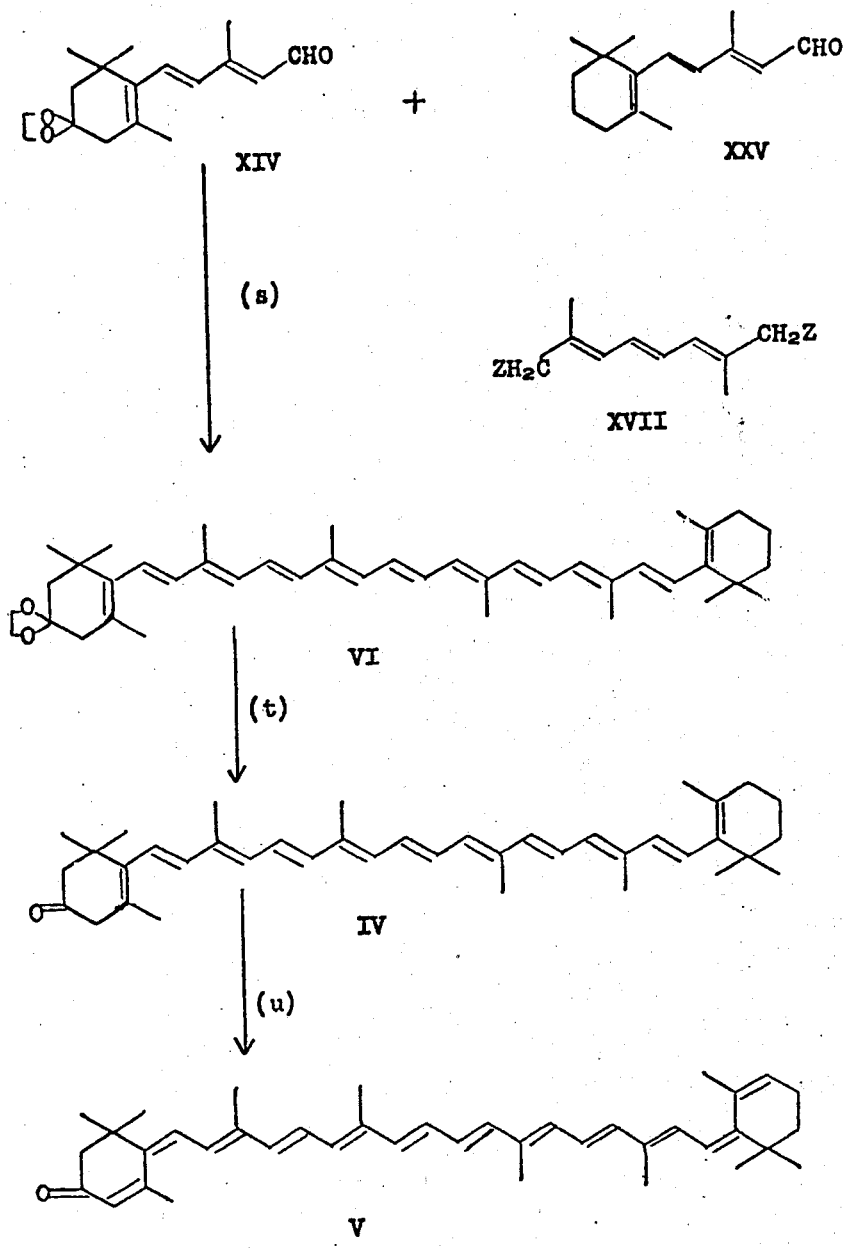

wherein Z is as above.

3,3-ethylenedioxy-trans-β-carotene (formula VI) can be prepared in step (s) from the compound of formula XIV by first reacting the compound of the formula XIV above with beta-ionylidene acetaldehyde (the compound of formula XXV) and the dipentavalent phosphorous compound of formula XVII above. The compound of formula VI above is produced by condensing 1 mole of the compound of formula XIV above with 1 mole of beta-ionylidene-acetaldehyde (formula XXV above) and 1 mole of the dipentavalent phosphorous compound of formula XVII above. This reaction can be carried out in the same manner and utilizing the same conditions as in step (k) where 2 moles of the compound of formula XIV above were reacted with the dipentavalent phosphorous formula XVII.

The compound of formula VI above can be converted into the compound of formula IV above by treating the compound of formula VI above with a mineral acid so as to convert the ethylene dioxy group to a keto group. Any conventional method of acid hydrolysis can be utilized to convert the compound of formula VI above to the compound of formula IV above. The acid hydrolysis of step (t) is carried out in an inert organic solvent medium. Any of the conventional organic solvents such as those hereinbefore mentioned can be utilized to carry out this reaction. Furthermore, any conventional inorganic mineral acid can be utilized to convert the compound of formula VI above to the compounds of formula IV. In carrying out this reaction, temperature and pressure are not critical and this reaction of step (t) can be carried out at room temperature or elevated temperatures, i.e., the reflux temperature of the solvent. If desired, elevated or reduced pressure can be utilized in carrying out this reaction. Generally, the compound of formula IV above is very unstable and should be isolated in a nitrogen atmosphere without any light. This is true since the presence of light or air will slowly oxidize the compound of formula IV above to the compound of formula V.

The conversion of the compound of the formula IV to dehydro aphanine is carried out by oxidizing the compound of formula IV with air or light in an inert organic solvent as in step (u). It has been found that by treating the compound of formula IV with air or light, an additional double bond is imparted to the compound with a shift of the original double bonds to the next position. In carrying out the reaction of step (u), any conventional inert organic solvent can be utilized as the reaction media. In carrying out the reaction of step (u), temperature and pressure are ot critical and this reaction can be carried out at room temperature. Furthermore, elevated or reduced temperatures can be utilized, if desired. Additionally, elevated or reduced pressures can be utilized in carrying out this reaction. Any conventional oxidizing conditions can be utilized. However, since compound IV oxidizes slowly to compound V in air or light, it is preferable to utilize standard oxidizing conditions in the reaction of step (u).

It has been found that the compound of formula IV and formula V above both impart to foodstuffs, pharmaceutical and cosmetic preparations a dark red color. The compound of formula IV above and V above can be utilized as a foodstuff, cosmetic and pharmaceutical coloring to impart a dark red color in the same manner as beta carotene.

The invention is further illustrated but not limited by the following Examples. In the examples, the petroleum ether utilized boiled at a range of 60°C. to 80°C. All temperatures utilized in the following examples are in degrees centigrade.

EXAMPLE 1

3,5,5-Trimethyl-2-Cyclohexen-1-on-4-Carboxylic Acid Methyl Ester

A mixture of 2.6 kg. of methyl acetoacetate, 2.75 kg. of mesityl oxide, 400 g. of zinc chloride, 2 l. of heptane, and 2 l. of benzene was refluxed for 5 days. The water formed during the reaction was azeotropically distilled off and collected in a separator. A brown oily produce remained in the flask. The oily product was then washed with water, sodium bicarbonate solution, and again with water. The oil which remained after washing was dried over calcium chloride and the heptane-benzene solvent removed under vacuum. The remaining oil was distilled under high vacuum over a packed column. From the distillation, there was obtained first a forecut of unreacted ethyl acetoacetate and mesityl oxide, a second fraction of isophorone by product and finally crude 3,5,5-trimethyl-2-cyclohexen-1-on-4-carboxylic acid methyl ester with a boiling range of 95° – 104° at 0.4 – 0.6 mm. Hg. This crude material was utilized for all experiments without further purification. Pure 3,5,5-trimethyl-2-cyclohexen-1-on-4-carboxylic acid methyl ester was obtained by chromatographic separation on silica gel G (finely divided powdered silica containing trace amounts of calcium sulfate) using petroleum ether and ethyl ether in a volume ratio of 7 to 3.

EXAMPLE 2

3,5,5-Trimethyl-2-Cyclohexen-1-on-4-Carboxylic Acid Ethyl Ester

This compound was prepared in the same manner as in Example 1 except ethyl acetoacetate was utilized in place of methyl acetoacetate.

EXAMPLE 3

2,6,6-Trimethyl-4-Ethoxy-1,3-Cyclohexadien-1-Carboxylic Acid Methyl Ester 800 g. of crude 3,5,5-trimethyl-2-cyclohexen-1-on-4-carboxylic acid methyl ester prepared in Example 1, and 720 g. of triethyl orthoformate were mixed with 1.5 l. of anhydrous ethanol containing 4 ml. of sulfuric acid. After standing for 4 hours at room temperature, the dark blue solution was poured onto petroleum ether over a sodium bicarbonate solution. The ether layer was washed twice with water, dried over sodium sulfate, and concentrated by removing all of the ether solvent. The resulting dark residue was distilled over a vigreux column under high vacuum to yield 2,6,6-trimethyl-4-ethoxy-1,3-cyclohexadien-1-carboxylic acid methyl ester.

EXAMPLE 4

7,9,9-Trimethyl-1,4-Dioxaspiro [4,5] dec-7-en-8-Carboxylic Acid Methyl Ester 670 g. of crude 2,6,6-trimethyl-4-ethoxy-1,3-cyclohexadien-1-carboxylic acid methyl ester and 185 g. of ethylene glycol were heated in 3 l. of benzene in the presence of 3 g. of p-toluene sulfonic acid. The reaction was stopped after 1.5 l. of benzene had distilled over. The cold solution was washed with sodium bicarbonate solution and water, dried, and evaporated. The remaining oil was identified as 7,9,9-trimethyl-1,4-dioxaspiro [4,5] dec-7-en-8-carboxylic acid methyl ester.

EXAMPLE 5

7,9,9-Trimethyl-1,4-Dioxaspiro [4,5] dec-7-en-8-Methanol

A solution of 300 g. of 7,9,9-trimethyl-1,4-dioxaspiro [4,5] dec-7-en-8-carboxylic acid methyl ester in 1 l. of ether was slowly added to a stirred suspension of 50 g. of lithium aluminum hydride in 1 l. of ethyl ether. During the addition, which required 1 hour, the temperature was kept between 15° and 20°. It was then allowed to climb to room temperature, and stirring under nitrogen was continued for 4 hours. After quenching the reaction by slow addition of 250 ml. of water at 5°–15°, the inorganic material was filtered by suction. The filtrate was dried over sodium sulfate and concentrated to yield a viscous oil which solidified on refrigeration. Recrystallization from ethyl ether-petroleum ether gave pure material. The material was analyzed as 7,9,9-trimethyl-1,4-dioxaspiro [4,5] dec-7-en-8-methanol.

EXAMPLE 6

7,9,9-Trimethyl-1,4-Dioxaspiro [4,5] dec-7-en-8-Carboxaldehyde 3 kg. of manganese dioxide was added in 4 portions over a period of 2 days to a solution of 150 g. of crystalline 7,9,9-trimethyl-1,4-dioxaspiro [4,5] dec-7-en-8-methanol in 3 l. of methylene chloride. After the mixture was stirred under nitrogen for an additional day, the oxidation was complete according to a determination by thin layer chromatagraphy. Filtration and evaporation of the solvent yielded the crude product which was used for the next step without further purification. A small portion of this product was purified by vacuum distillation. This product was identified as 7,9,9-trimethyl-1,4-dioxaspiro [4,5] dec-7-en-8-carboxaldehyde.

EXAMPLE 7

3-Ethylenedioxy-β-Ionone

A mixture of 120 g. of crude 7,9,9-trimethyl-1,4-dioxaspiro [4,5] dec-7-en-8-carboxaldehyde, 500 ml. of acetone, and 60 ml. of 10 percent aqueous solution of potassium hydroxide was refluxed under nitrogen for 16 hours. Most of the solvent was removed under vacuum and the residue was diluted with water and extracted with petroleum ether leaving an oil layer. The oil layer was washed neutral with water, dried over sodium sulfate, and concentrated. The residue was distilled under reduced pressure over a vigreux column. The fraction boiling between 115° and 140 at 0.3 to 0.7 mm. Hg. crystallized from petroleum ether at −10° to −20°. Recrystallization from petroleum ether yielded 60 g. of the 3-ethylenedioxy-β-Ionone.

EXAMPLE 8

5-(4-Ethylenedioxy-2,6,6-Trimethyl-1-Cyclohexen-1-yl)-3-Methyl-2,4-Pentadienoic Acid Ethyl Ester 90 g. of α-diethyl phosphone-ethyl acetate was added to a suspension of 16 g. of sodium amide in 500 ml. of dry ether, and the mixture was stirred for 4 hours. 51 g. of crystalline 3-ethylenedioxy-β-ionone dissolved in 200 ml. ether was then added within 15 min., and the mixture was stirred under nitrogen for 18 hours at room temperature. The reaction was quenched with ice water and extracted with petroleum ether. The petroleum-ether layer was washed neutral with water, dried over sodium sulfate, and concentrated after filtration through aluminum oxide to yield a colorless oil which was identified as 5-(4-ethylenedioxy 2,6,6-trimethyl-1-cyclohexen-1-yl)-3-methyl-2,4-pentadienoic acid ethyl ester.

EXAMPLE 9

5-(4-Ethylenedioxy-2,6,6-Trimethyl-1-Cyclohexen-1-yl)-3-Methyl-2,4-Pentadienol A solution of 50 g. of crude 5-(4-ethylenedioxy-2,6,6-trimethyl-1-cyclohexen-1-yl)-3-methyl-2,4-pentadienoic acid ethyl ester in 200 ml. of diethyl ether was added over a period of 30 minutes to a suspension of 7.5 g. of lithium aluminum hydride in 150 ml. of diethyl ether at −10° to 0°. Stirring at 0° to 5° was then continued for 2 hours. AFter this period, the reaction was quenched with 40 ml. of water which was dropped in slowly to keep the temperature below 15°. The inorganic material, which was present in the reaction was a solid, was filtered by suction, and the filtrate was dried and concentrated under vacuum to yield a colorless viscous oil. This produce was identified as 5-(4-ethylenedioxy-2,6,6-trimethyl-1-cyclohexen-1-yl)-3-methyl-2,4-pentadienol.

EXAMPLE 10

5-(4-Ethylenedioxy-2,6,6-Trimethyl-1-Cyclohexen-1-yl)-3-Methyl-2,4-Pentadienal 500 g. of manganese dioxide was added in 3 portions over 9 hours to a solution of 42 g. of crude 5-(4-ethylenedioxy-2,6,6-trimethyl-1-cyclohexen-1-yl)-3-methyl-2,4-pentadienol in 1 l. of benzene. During this period a suspension formed. The suspension was then stirred under nitrogen for 24 hours. Filtration and evaporation of the solvent yielded a light yellow oil which was used for the next steps without further purification. The yellow oil was purified by chromatography on silica gel G. The yellow oil was identified as 5-(4-Ethylenedioxy-2,6,6-trimethyl-1-cyclohexen-1-yl)-3-methyl-2,4-pentadienal.

EXAMPLE 11

3,3,3′,3′-Bis (ethylenedioxy)-trans-β-carotene

A. 2.5 g. of sodium methoxide was added over 1 hour at 0°–5° to a solution containing 6 g. of 5-(4-ethylenedioxy-2,6,6-trimethyl-1-cyclohexen-1-yl)-3-methyl-2,4-pentadienal and 7.5 g. of 2,7-dimethyl-2,4,6-octatrienylene bis(triphenyl-phosphonium bromide) dissolved in 50 ml. of methanol. After the addition, the resulting mixture was stirred under nitrogen for 2 hours. After this period, 2 g. more of this phosphonium bromide salt and another 0.5 g. of sodium methoxide were added to the mixture. Stirring was continued for an additional 4 hours at 0°–5°. The precipitated carotene was collected, washed with methanol and water, and recrystallized from benzene-methanol solvent mixture. This product was identified as 3,3,3′,3′-Bis(ethylenedioxy)-trans-β-carotene.

B. 4 g. of potassium-t-butoxide was added to a stirred solution of 9.5 g. of 1,8-bis-diethyl phosphone-2,7-dimethyl-2,4,6-octatriene in 100 ml. of benzene. After 10 min., 4.5 g. of 5-(4-ethylenedioxy-2,6,6-trimethyl-1-cyclohexen-1-yl)-3-methyl-2,4-pentadienal dissolved in 25 ml. of benzene was dropped in. Five minutes later, 4 g. more of potassium-t-butoxide followed by another 4.5 g. of the pentadienal was added. The mixture was stirred at room temperature for 1 hour, quenched with ice water, and extracted with a mixture of petroleum ether and benzene. The organic phase was washed neutral with 90 percent aqueous methanol and water, dried over sodium sulfate, and concentrated. The carotenoid crystallized from the residue in acetone methanol solvent. This product was identified as 3,3,3',3'-bis (ethylenedioxy)-trans-β-carotene.

EXAMPLE 12

3,3'-Dioxo-trans-β-carotene, (beta-beta diketo carotene)

2 g. of 3,3,3',3'-bis (ethylenedioxy)-trans-β-carotene, 60 ml. of methylene chloride, 60 ml. of acetone, and 12 ml. of 10 percent aqueous sulfuric acid were refluxed under nitrogen for 3½ hours. The carotenoid was extracted from the reaction mixture with methylene chloride after dilution with water. The extracts were collected and washed with water and sodium bicarbonate solution and water, dried over sodium sulfate, and concentrated. 3,3'-dioxo-trans-β-carotene (beta-beta diketo carotene) contaminated with 3,3'-dioxo-trans-α-carotene (alpha beta diketo carotene) crystallized from an aceton methanol solvent mixture. 3,3'-dioxo-trans-β-carotene was separated from 3,3'-dioxo-trans-α-carotene by chromatography. This was accomplished by passing 9 parts by volume diethylene chloride and 1 part by volume of diethyl ether containing the mixture of 3,3'-dioxo-trans-α-carotene and 3,3'dioxo-trans-β-carotene dissolved therein through column containing 60 times by weight of the mixture of silica gel. The 3,3'-dioxo-trans-α-carotene was more strongly adsorbed in the column than the 3,3'-dioxo-trans-β-carotene, and hence the 3,3'-dioxo-trans-β-carotene came down the column faster than 3,3'-dioxo-trans-α-carotene. Hence the first fractions collected contained all 3,3'-dioxo-trans-β-carotene. The later fractions which were flushed out with methylene chloride-diethyl ether solvent contained all 3,3'-dioxo-trans-βcarotene. The 3,3'-dioxo-trans-β-carotene was crystallized from a mixed methanol-benzene solvent. The crystallized material from the first fractions were identified as pure 3,3'-dioxo-trans-β-carotene.

EXAMPLE 13

3.3'-Dioxo-trans-α-Carotene 3,3'-dioxo-trans-α-carotene as well as 3,3'-dioxo-trans-β-carotene was formed during the hydrolysis of 3,3'-bis-ethylene-dioxy-β-carotene. 3,3'-dioxo-trans-α-carotene was more strongly absorbed on the silica gel column than 3,3'-dioxo-trans-β-carotene from which it was eluted in the above chromatogram. It crystallized readily from methanol benzene solvent mixture in red plates with a metallic lustre. The crystallized material was identified as 3,3'-dioxo-trans-α-carotene.

EXAMPLE 14

3,7,12,16-Tetramethyl-1,18-bis(2,6,6-trimethyl-4-oxo-2-cyclohexen-1-yl) 1,3,5,7,9,11,13,15,17-octadecanonaene (Alpha-Alpha Diketo Carotene)

0.5 g. of 3,3,3',3'-bis-ethylenedioxy-trans-β-carotene, 50 ml. of methylene chloride, 25 ml. of ethanol, 1 ml. of water, and 2 ml. of 36 percent by weight hydrochloric acid were allowed to stand at room temperature for 5 hours. After dilution with water, the carotene was extracted with methylene chloride. The extracts were washed neutral, dried and concentrated. The residue crystallized from solvent mixture containing methanol and benzene in a volume ratio of 1 to 1. The residue was dissolved in a solvent mixture comprising diethyl ether and methylene chloride in a volume ratio of 1 to 9 and the solution was subjected to chromatography to separate the small amount of 3,3'-dioxo-trans-α-carotene which formed during the reaction. Chromatography was performed in a silica gel column in the manner described in Example 12. The alpha alpha diketo carotene was easily separated from the faster traveling 3,3-dioxo-trans-α-carotene due to the fact that alpha alpha diketo carotene is more strongly absorbed on silica gel than the 3,3' -dioxo-trans-α-carotene. The separated alpha alpha diketo carotene was crystallized easily from methanol benzene solvent mixture. This compound was identified as 3,7,12,16-tetramethyl-1,18-bis(2,6,6-trimethyl-4-oxo-2-cyclohexen-1-yl) 1,3,5,7,9,11,13,15,17-octadecanonaene.

EXAMPLE 15

2,6,6-Trimethyl-4-Ethoxy-1,3-Cyclohexadien-1-Carboxaldehyde 250 g. of crude 2,6,6-trimethyl-4-ethoxy-1,3-cyclohexadien-1-carboxylic acid methyl ester, prepared in Example 3, was added over a 1-hour period to a suspension of 50 g. of lithium aluminum hydride in 1 l. of diethyl ether at a temperature of 10°–15°. Stirring of the reaction mixture at this temperature was continued for an additional 4 hours. The reaction mixture after this period was quenched by slow addition of 250 ml. of water while the temperature was kept below 15°. The inorganic material was filtered by suction and the filtrate was washed well with diethyl ether. The filtrate was dried over sodium sulfate and concentrated under vacuum at 20°–30° to yield crude 2,6,6-trimethyl-4-ethoxy-1,3-cyclohexadien-1-methanol as a viscous oil.

210 grams of this crude reduction product was oxidized with 3 kg. of manganese dioxide in 3 l. of benzene containing 0.5 percent pyridine. The manganese dioxide was added in 3 portions over an 8-hour period. After stirring for an additional 24 hours under nitrogen a suspension formed, this suspension was filtered, the filtrate was concentrated, and the remaining yellow oil was distilled over a vigreux column under reduced pressure to yield 2,6,6-trimethyl-4-ethoxy-1,3-cyclohexadien-1-carboxaldehyde.

EXAMPLE 16

3-Ethoxy-3,4-Dehydro-β-Ionone 40 g of 2,6,6-trimethyl-4-ethoxy-1,3-cyclohexadien-1-carboxaldehyde, 400 ml. of acetone, and 80 ml. of a 10 percent aqueous solution of potassium hydroxide were refluxed under nitrogen for 4 days. After this period, the bulk of the solvent was removed and the residue was diluted with water and extracted with petroleum ether solvent. The extract was distilled to remove the solvent and a brown oil was obtained. The brown oil was distilled over a vigreux column under high vacuum. The material boiling between 105° and 125° at 0.2 to 0.4 mm. Hg. (23 g.) crystallized partially at about 0°C. and melted after recrystallization from a concentrated methanolic solution at 43°–45°. This product was identified as 3-ethoxy-3,4-dehydro-β-ionone.

EXAMPLE 17

5-(2,6,6-Trimethyl-4-Ethoxy-1,3-Cyclohexadien-1-yl)-3-Methyl-2,4-Pentadienoic Acid Ethyl Ester 22 g. of α-diethyl phosphone-ethyl acetate was added to 4 g. of sodium amide in 150 ml. of dry ether, and the suspension was stirred for 3 hours under nitrogen. 12 g. of crystalline 3-ethoxy-3,4-dehydro-β-ionone dissolved in 50 ml. of diethyl ether was added in, and the mixture was refluxed for 18 hours. As the reaction showed unreacted ionone by submitting a sample to thin layer chromatography, 10 g. more of the phosphone ethyl acetate together with 2.3 g. of sodium amide was added and refluxing was continued for an additional 24 hours. The cold mixture was poured on ice water and extracted with petroleum ether. After distilling off the petroleum ether, a yellow oil remained. The product was identified as 5-(2,6,6-trimethyl-4-ethoxy-1,3-cyclohexadien-1-yl)-3-methyl-2,4-pentadienoic acid ethyl ester.

EXAMPLE 18

5-(2,6,6-Trimethyl-4-Ethoxy-1,3-Cyclohexadien-1-yl)-3-Methyl-2,4-Pentadienal

A solution of 14 g. of crude 5-(2,6,6-trimethyl-4-ethoxy-1,3-cyclohexadien-1-yl)-3-methyl-2,4-pentadienoic acid ethyl ester in 50 ml. of diethyl ether was added to a suspension of 1.5 g. of lithium aluminum hydride in 100 ml. of ether at −10° to −5°. Stirring at this temperature was continued for 2 hours. After this period, the reaction was hydrolyzed by the slow addition of 10 ml. of water. The aluminum hydroxide was filtered by suction. The filtrate was dried over sodium sulfate and was concentrated under vacuum, and the residue was oxidized by the addition of 150 g. of manganese dioxide in 300 ml. of benzene containing 1 percent pyridine. After the addition, the mixture was allowed to stand for 18 hours. After this period, all of the solid inorganic material present in this mixture was filtered. Evaporation of the filtered solution yielded a brown oil which was identified as 5-(2,6,6-trimethyl-4-ethoxy-1,3-cyclohexadien-1-yl)- 3-methyl-2,4-pentadienal.

EXAMPLE 19

3,3′-Diethoxy-3,3′,4,4′-Tetradehydro-trans-β-Carotene 1 g. of potassium-t-butoxide was added to a solution of 4 g. of crude 1,8-bis-diethyl phosphone-2,7-dimethyl-2,4,6-octatrien in 50 ml. of benzene. After the mixture was stirred 10 min. under nitrogen, 2.5 g. of crude 5-(2,6,6-trimethyl-4-ethoxy-1,3-cyclohexadien-1-yl)-3-methyl-2,4-pentadienal was added. Five minutes later, a second portion of 1 g. of potassium-t-butoxide, followed by an addition of 2.5 g. of the 2,4-pentadienal was added to the reaction mixture and the mixture was stirred for an additional 15 min. After this period, the mixture was diluted by the addition of petroleum ether. After dilution, the reaction mixture was quenched with ice water. After quenching two layers formed, i.e., a water layer and a petroleum ether-benzene layer. The ether benzene layer was separated and was washed with water, 90 percent aqueous methanol and water, and dried over sodium sulfate, and concentrated to yield 3,3′-diethoxy-3,3′,4,4′-tetradehydro-trans-β-carotene in the form of crystals.

EXAMPLE 20

Zeaxanthin 1.5 g. of 3,3′-dioxo-trans-β-carotene dissolved in 200 ml. of methylene chloride and 100 ml. of methanol was reduced with 1 g. of sodium borohydride at 0°–5° for 3½ hours. The solution was washed 4 times with water, dried over sodium sulfate, and concentrated forming a crystalline residue. The crystalline residue was recrystallized from benzene ethanol to give zeaxanthin.

EXAMPLE 21

Xanthophyll 0.1 of 3,3′-dioxo-trans-α-carotene in 50 ml. of methylene chloride and 25 ml. of methanol was reduced with 0.2 g. of sodium borohydride for 5 hours at room temperature. After this period, the remaining solution was washed 3 times with water and the water layer removed. The remaining organic layer was concentrated to yield crystalline xanthophyll.

EXAMPLE 22

3-Ethylenedioxy-trans-β-Carotene

The condensation of 5 g. of crude 1,8-bis-diethyl phosphone-2,7-dimethyl-2,4,6-octatriene with a mixture of 2 g. of β-ionylideneacetaldehyde and 3 g. of 51(4-ethylene-dioxy-2,6,6-trimethyl-1-cyclohexen-1-yl)-3-methyl-2,4-pentadienal was done as in Example 19 with 3 g. of potassium-t-butoxide in 50 ml. of benzene. 3-ethylene dioxy-trans-β-carotene crystallized from petroleum ether in the manner of Example 19.

EXAMPLE 23

3,5,5-4-[18-(2,6,6-trimethylcyclohexenyl)-3,7,12,16-tetramethyl-octadeca-1,3,5,7,9,11,13,15,17-nonaenyl]-3-cyclohexen-1-one (Aphanin)

0.3 g. of 3-ethylenedioxy-trans-β-carotene, 50 ml. of methylene chloride, 50 ml. of acetone, and 10 ml. of 10 percent aqueous sulfuric acid were refluxed for 4 hours under nitrogen.

The reaction mixture was extracted with methylene chloride after dilution with water. The extracts were collected and washed with water, sodium bicarbonate solution and water, dried over sodium sulfate, and concentrated to form a residue. The residue was crystallized from 50 parts by volume acetone-50 parts by volume methanol solvent mixture. The crystalline material was dissolved in methylene chloride and subjected to chromatography in a silica gel G column to remove any isomers. The product was identified as 3,5,5-4-[18-(2,6,6-trimethyl-cyclohexenyl)-3,7,12,16-tetramethyloctadeca-1,3,5,7,9,11,13,15,17-nonaenyl]-3-cyclohexen-1-one.

EXAMPLE 24

3,5,5-Trimethyl-4-[18-((2,6,6-trimethyl-2-cyclohexen-1-ylidenyl)-3,7,12,16-tetramethyl-octadeca-2,4,6,10,12,14,16-octaenylidenyl]-2-cyclohexen-1-one (Dehydro-aphanin)

Dehydrogenation of 3-aphanin was noticed to occur during chromatography. The violet-red oxidation product was eluted after aphanin and rechromatographed on silica gel G using benzene-ethyl ether solvent in a ratio of 9 to 1.

EXAMPLE 25

3,7,12,16-Tetramethyl-1,18-bis(2,6,6-trimethyl-4-oxo-2-cyclohexen-1-yl) 1,3,5,7,9,11,13,15,17-octadecanonaene (Alpha-Alpha Diketo Carotene 3,3′-diethoxy-3,3′,4,4′-tetradehydro-trans-β-carotene is converted to alpha-alpha diketo carotene by acid hydrolysis in the same manner as 3,3,3',3'-bis ethylene dioxy-trans-β-carotene in Example 14.
EXAMPLE 26
ε-Zeaxanthin
Alpha-Alpha diketo carotene is reduced with sodium borohydride to form ε-zeaxanthin utilizing the same procedure as in Example 20.
We claim:
1. A compound of the formula:
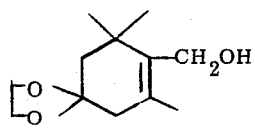
* * * * *